United States Patent
Yu et al.

(10) Patent No.: US 11,015,193 B2
(45) Date of Patent: May 25, 2021

(54) sgRNA AND METHOD FOR SPECIFICALLY ACTIVATING HUMAN RSPO2 GENE WITH CRISPR-CAS9 AND APPLICATION THEREOF

(71) Applicant: The First Hospital of Jiaxing, Zhejiang (CN)

(72) Inventors: Linghua Yu, Zhejiang (CN); Ming Yao, Zhejiang (CN)

(73) Assignee: The First Hospital of Jiaxing, Zhejiang (CN)

( * ) Notice: Subject to any disclaimer, the term of this patent is extended or adjusted under 35 U.S.C. 154(b) by 0 days.

(21) Appl. No.: 15/964,024

(22) Filed: Apr. 26, 2018

(65) Prior Publication Data
US 2018/0273939 A1 Sep. 27, 2018

(30) Foreign Application Priority Data
Dec. 7, 2017 (CN) .......................... 201711286245.5

(51) Int. Cl.
*C12N 15/11* (2006.01)
*C12N 9/22* (2006.01)
*C12N 15/113* (2010.01)

(52) U.S. Cl.
CPC ................ *C12N 15/11* (2013.01); *C12N 9/22* (2013.01); *C12N 15/1138* (2013.01); *C12N 2310/20* (2017.05); *C12N 2330/51* (2013.01); *C12N 2740/15043* (2013.01)

(58) Field of Classification Search
None
See application file for complete search history.

(56) References Cited

PUBLICATIONS

GenBank Accession No. AP003479 "*Homo sapiens* genomic DNA, chromosome 8q23, clone: KB1296F8" (Year: 2001).*

* cited by examiner

*Primary Examiner* — Rebecca E Prouty

(57) ABSTRACT

A method of constructing a specific CRISPR-Cas9 (Clustered Regularly Interspaced Short Palindromic Repeats associated) to activate a RSPO2 (R-spondin 2) gene is disclosed in the present invention. The method comprises the following steps: designing a sgRNA (single guide RNA) of a specifically targeted human RSPO2 gene; constructing a CRISPR-Cas9 recombinant lentivirus vector of a specifically activated RSPO2 gene; and lentiviral packaging a CRISPR-Cas9 system of the specifically activated RSPO2 gene. The CRISPR-Cas9 system designed by the present invention activates the RSPO2 target gene expression and promotes the activation of the hepatic stellate cell.

1 Claim, 4 Drawing Sheets
Specification includes a Sequence Listing.

1#　　SEQ ID NO:38　　　　　　　　　　　　　　　　Target sequence
5`-TTCGATTTCTTGGCTTTATATATCTTGTGGAAAGGACGAAA<u>CACCGCAACGTTCTTTAGGACCTC</u>GTTTTAGA
GCTAGGCCAACATGAGGATCACCCATGTCTGCAGGGCCTAGCAAGTTAAAATAAGGCTAGTCCGTTATCAACTTG
GCCAACATGAGGATCACCCATGTCTGCAGGGCCAAGTGGCACCGAGTCGGTGCTTTTTTTGGATCCTGCAAAGA
TGGATAAAGTTTTAAACAGAGAGGAATCTTTGCAGCTAATGGACCTTCTAATTGGCTCCGGTG---GGCC-3`

2#　　SEQ ID NO:39　　　　　　　　　　　　　　　　Target sequence
5`-TTCGATTCTTGGCTTTATATATCTTGTGGAAAGGACGAAA<u>CAACGTTTAGGACCTCAGGGAAAC</u>GTTTTAGA
GCTAGAAATAGCAAGTTAAAATAAGGCTAGTCCGTTATCAACTTGAAAAAGTGGCACCGAGTCGGTGCTTTTTT
GTTTTAGAGCTAGAAATAGCAAGTTAAAATAAGGCTAGTCCGTTTTTAGCGCGTGCGCCAATTCTGCAGACAAAT
GGCTCTAGAGGTACCCGTTACATAACTTACGGTAAATGGCCCGCCTGGCTGACCGCCCAACGA---GTCCA-3`

3#　　SEQ ID NO:40　　　　　　　　　　　　　　　　Target sequence
5`-TTCGATTTCTTGGCTTTATATATCTTGTGGAAAGGACGAAA<u>CACCGTTTAGGACCCAGGAACTCC</u>GTTTTAGA
GCTAGAAATAGCAAGTTAAAATAAGGCTAGTCCGTTATCAACTTGAAAAAGTGGCACCGAGTCGGTGCTTTTTT
GTTTTAGAGCTAGAAATAGCAAGTTAAAATAAGGCTAGTCCGTTTTTAGCGCGTGCGCCAATTCTGCAGACAAAT
GGCTCTAGAGGTACCCGTTACATAACTTACGGTAAATGGCCCGCCTGGCTGACCGCCCAACGAC---AGGC-3`

Fig. 2

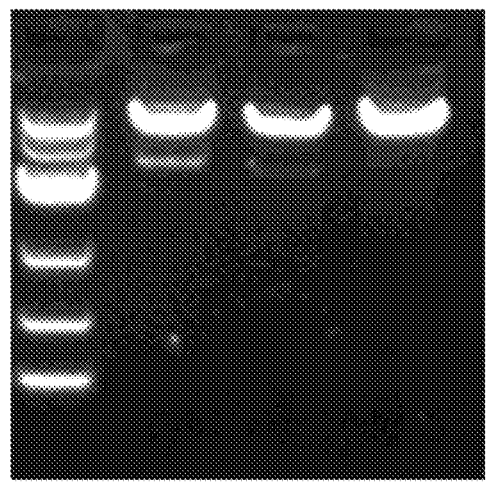

Fig. 3

1# SEQ ID NO:41    Target sequence

5`-CGATTTCTTGGCTTTATATATCTTGTGGAAAGGACGAAA<u>CACCGCAACGTTCTTTAGGACCTC</u>GTTTTAGAG
CTAGGCCAACATGAGGATCACCCATGTCTGCAGGGCCTAGCAAGTTAAAATAAGGCTAGTCCGTTATCAACTTG
GCCAACATGAGGATCACCCATGTCTGCAGGGCCAAGTGGCACCGAGTCGGTGCTTTTTTTGGATCCTGCGTATT
TCGGTTTTTGGGGCCGCGGGCGGCGACGGGGCCCGTGCGTCCCAGCGCACATGTTCGGC---GCCT-3`

2# SEQ ID NO:42    Target sequence

5`-
CGATTTCTTGGCTTTATATATCTTGTGGAAAGGACGAAA<u>CAACGTTTAGGACCTCAGGGAAAC</u>GTTTTAGAG
CTAGGCCAACATGAGGATCACCCATGTCTGCAGGGCCTAGCAAGTTAAAATAAGGCTAGTCCGTTATCAACTTG
GCCAACATGAGGATCACCCATGTCTGCAGGGCCAAGTGGCACCGAGTCGGTGCTTTTTTTGGATCCTGCGTATT
TCGGTTTTTGGGGCCGCGGGCGGCGACGGGGCCCGTGCGTCCCAGCGCACATGTTCGGC---GCCT-3`

3# SEQ ID NO:43    Target sequence

5`-CGATTTCTTGGCTTTATATATCTTGTGGAAAGGACGAAA<u>CACCGTTTAGGACCCAGGAACTC</u>GTTTTAGAG
CTAGGCCAACATGAGGATCACCCATGTCTGCAGGGCCTAGCAAGTTAAAATAAGGCTAGTCCGTTATCAACTTG
GCCAACATGAGGATCACCCATGTCTGCAGGGCCAAGTGGCACCGAGTCGGTGCTTTTTTTGGATCCTGCGTATT
TCGGTTTTTGGGGCCGCGGGCGGCGACGGGGCCCGTGCGTCCCAGCGCACATGTTCGGC---GCCT-3`

Fig. 4

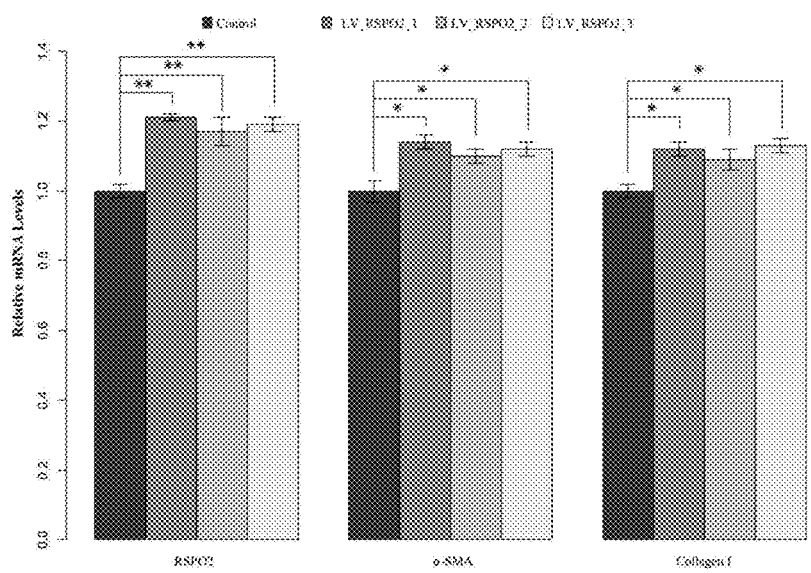

Fig. 5 sgRNA AND METHOD FOR SPECIFICALLY ACTIVATING HUMAN RSPO2 GENE WITH CRISPR-CAS9 AND APPLICATION THEREOF

CROSS REFERENCE OF RELATED APPLICATION

This application claims priority under 35 U.S.C. 119(a-d) to CN 201711286245.5, filed Dec. 7, 2017.

BACKGROUND OF THE PRESENT INVENTION

Field of Invention

The present invention relates to the biotechnology field, and more particularly to a method of constructing the specific CRISPR-Cas9 to activate RSPO2 gene and applications thereof.

Description of Related Arts

The CRISPR-Cas9 (Clustered Regularly Interspaced Short Palindromic Repeats associated) widely exists in bacteria and archaea, which is a RNA-guided heritable adaptive immunity system. CRISPR (Clustered Regularly Interspaced Short Palindromic Repeats) is composed of highly conserved repeats and multiple spacers which are arranged in order. A length of the repeats is 21-48 bp. The repeats is spaced by spacers of 26-72 bp. Cas9 (CRISPR associated) is a double stranded DNA nuclease which comprises two domains: 1) HNH-like domain cuts the DNA strand complementary to the crRNA (CRISPR RNA); 2) RuvC-like domain cut non-complementary strand. The basic mechanism of the CRISPR-Cas9 is as follow 1) transcribing and processing the CRISPR sequence into crRNA; 2) recruiting Cas9 protein by tracrRNA (trans-activating crRNA); 3) matching the spacers of crRNA with the neighboring target of PAM (Protospacer Adjacent Motif) to instruct Cas9 protein to cut the target.

The specificity of editing the target sequence by CRISPR is realized by the complementary identification of the target sequence. The tracrRNA and crRNA are expressed as a sgRNA (single guide RNA). The CRISPR-Cas9 system is simplified as Cas9 protein and sgRNA, which is easy to construct and with high efficiency and low cost. The simplified CRISPR-Cas9 system is a most suitable choice for gene editing. To design a sgRNA specifically binding with target sequence is the key technology of the CRISPR-Cas9 system.

The two domains of Cas9 are deactivated by engineering the Cas9 protein to form the dCas9 which is able to combine the target sequence and the sgRNA but unable to cut DNA. The dCas9 is further merged with the transcription-regulation protein (VP64, P65, HSF1) to specifically activate (CRISPR activation, CRISPRa) the target gene expression.

Liver fibrosis is a reversible wound-healing response to a variety of insults. With chronic liver injury, this wound-healing process is presented as a progressive substitution of the functional parenchyma by scar tissue. The pathological characteristics are that various compositions, mainly collagen, of the extracellular matrix are synthesized and increased while the degradation is relatively insufficient and the interlobular septa are not formed. Further development leads to cirrhosis. The liver fibrosis is reversible. A prevention and early intervention to the liver fibrosis is the best practice to stable the condition and prevent the liver fibrosis from developing into cirrhosis and liver cancer.

As the key fibrogenic cell population of the liver, the HSC (Hepatic Stellate Cell) is the primary cell type responsible for extracellular matrix synthesis and degradation. HSC activation and phenotypic switch to a myofibroblast-like cell is the central event of liver fibrogenesis. Many signaling pathways are implicated in HSC activation, perpetuation, and resolution, among which the Wnt pathway plays a pivotal role. Research shows that the Wnt signal pathway affects a competence of the hepatic stellate cell and the blockage of the Wnt signal pathway suppresses the HSC proliferation and induces the hepatic stellate cell death. Because the Wnt signal pathway participates in various biological processes including the differentiation and maintenance of the cell form and function, immunity, and cell carcinogenesis and death, a direct blockage of the Wnt signal path may causes adverse biological effects. RSPO2 (R-spondin2) is an important newly discovered regulation factor of the Wnt signal factor, which is able to activate and strengthen the Wnt/β-catenin signal pathway and play an important role in tissue differentiation, organogenesis and diseases.

To regulate the competence of hepatic stellate cell without blocking the important signal pathway such as Wnt directly is a pressing problem needs to be solved.

SUMMARY OF THE PRESENT INVENTION

An object of the present invention is to provide a method to activate the human RSPO2 gene with CRISPR specificity and strengthen the Wnt/β-catenin signal pathway to achieve the hepatic stellate cell competence. The present invention provides a new way to study the mechanism of liver fibrosis. The present invention designs and synthesizes a sgRNA of the specific target RSPO2 in the activated human RSPO2 gene by CRISPR-Cas9 specificity. The sgRNA is connected to the lentiviral vector and is packaged as lentivirus.

The technical solution to solve the problem is as follows:
First constructing a specific CRISPR-Cas9 to activate a RSPO2 gene, comprising steps of:
1.1) designing a sgRNA (single guide RNA) specifically targeted human RSPO2 gene;
1.11) designing the sgRNA of the targeted human RSPO2 gene; wherein the sgRNA satisfies following conditions
a) a length of the sgRNA is 20 nucleotide sequences;
b) a target of the sgRNA on the RSPO2 gene locates in a promoter region;
c) no research indicates how a relative position of sgRNA targeting to a TSS (transcription start site) affects an efficiency of transcriptional activation; based on an early stage experiment, the target is located on an upstream −120-−75 bp of the TSS;
d) 5'-NGG is selected for PAM in a RSPO promoter region;
e) a sgRNA target sequence is preferred to start at G to ensure an effective U6 promoter of a vector; and
f) a format of the sgRNA target sequence is as follows:
5'-G-(19N)-NGG-3' (the sgRNA target sequence starts at G)
or 5'-(20N)-NGG-3' (the sgRNA target sequence doesn't start at G)
wherein, 19N or 20N denotes 19 or 20 nucleotide sequences of the sgRNA target;
1.12) selecting the sgRNA of the targeted human RSPO2 gene; wherein a BLAST (Basic Local Alignment Search Tool) is adopted in a NCBI (National Center for Biotechnology Information) database to ensure a uniqueness of the sgRNA target sequence which is not paralogous with gene sequences other than the human RSPO2 gene; the sgRNA satisfies the following conditions:
a) the sgRNA target locates in DHSs (DNase I hypersensitive sites);
b) the sgRNA target locates in the upstream −120−−75 bp of the TSS;
c) a low off-target rate;
three sgRNA sequences corresponding to the different locus of RSPO2 gene are screened, which are shown in the Table 1:
table sgRNA sequences corresponding to the different locus of RSPO2 gene

| Target number | Target sequence | PAM | corresponding TSS position of the target |
|---|---|---|---|
| 1 | 5'-CAACGTTCTTTA GGACCTCA-3' (SEQ ID NO: 1) | GGG | −118 |
| 2 | 5'-TTTAGGACCTCA GGGAAACC-3' (SEQ ID NO: 3) | GGG | −110 |
| 3 | 5'-TTTAGGACCCAG GAACTCCG-3' (SEQ ID NO: 1) | AGG | −76 |

1.2) constructing a CRISPR-Cas9 recombinant lentivirus vector for specifically activating RSPO2 gene;
1.21) constructing sgRNA oligo, further comprising the following sub-steps:
a) adding a CACC (complementary sequence of BsmBI cutting site sticky ends) and a G (to ensure an effective U6 promoter) on a 5' end of a corresponding DNA sequence to obtain a forward oligo based on a selected sgRNA;
b) obtaining a complementary strand of a corresponding DNA based on the selected sgRNA; adding an AAAC (complementary sequence of BsmBI cutting site sticky ends) on the 5' end of the corresponding DNA sequence and adding a C on a 3' end to obtain a reverse oligo;
c) obtaining a oligonucleotides format as follow:
forward: 5'-CACC-G-(20N)-3';
reverse: 5'-AAAC-(20N)-C-3'; and
d) synthesizing the forward oligo and the reverse oligo respectively as shown in table 2;
table 2 oligonucleotides sequence of the sgRNA target sequence that specifically activates human RSPO2 gene

| Oligonucleotides | Oligonucleotides sequence |
|---|---|
| forward oligo(1) | 5'-CACCGCAACGTTCTTTAGGACCTCA-3' (SEQ ID NO: 23) |
| reverse oligo(1) | 5'-AAACTGAGGTCCTAAAGAACGTTGC-3' (SEQ ID NO: 24) |
| forward oligo(2) | 5'-CAACGTTTAGGACCTCAGGGAAACC-3' (SEQ ID NO: 25) |
| reverse oligo(2) | 5'-AAACGGTTTCCCTGAGGTCCTAAAC-3' (SEQ ID NO: 26) |

-continued

| Oligonucleotides | Oligonucleotides sequence |
|---|---|
| forward oligo(3) | 5'-CACCGTTTAGGACCCAGGAACTCCG-3' (SEQ ID NO: 27) |
| reverse oligo(3) | 5'-AAACCGGAGTTCCTGGGTCCTAAAC-3' (SEQ ID NO: 28) |

1.22) verifying the efficiency of the sgRNA;
wherein a synthesized oligonucleotides single-chain fragment is annealed and connected to PX458 vector plasmid (Feng zhang, Nature Protocol 2013); PX458 contains a Cas9 and a sgRNA backbone; a PX458 vector transcribes a sgRNA of the specifically targeted RSPO2 gene and a Cas9 protein that cuts the target inside a cell; further annealing and connecting sub-steps are as follow:
a) phosphorylating the oligonucleotides;
b) annealing and connecting the oligonucleotides to the vector;
c) plasmid transforming into-*Escherichia coli* DH5a;
d) screening a positive clone and identifying a sequence of a screened positive clone; wherein further sub-steps are as follow:
i) selecting a colony for PCR (Polymerase chain reaction) and initially identifying a positive clone; and
ii) sequence analyzing the screened positive clone; and
e) transfecting 29FT cell; amplifying the RSPO2 gene by PCR; identifying a T7EI enzyme digestion.
1.23) linearizing and recovering the vector; wherein a lentiviral vector adopts a lenti sgRNA(MS2)_zeo backbone (Feng Zhang, Nature, 2014); the lentiviral vector contains a BsmBI cutting site for inserting the sgRNA and an U6 promoter to control sgRNA expression;
wherein the lenti sgRNA(MS2)_zero backbone is adopted as a BmsBI cutting vector; a DNA purification kit is adopted to purify and recover an enzyme digestion product;
1.24) phosphorylating, annealing and connecting the oligonucleotides to the lenti sgRNA(MS2)_zeo backbone; wherein an annealing and connecting process in the step 1.24) further comprises steps of:
a) annealing a phosphorylated product of the forward oligo and reverse oligo to generate fragments with BsmBI cohesive ends; and
b) connecting the fragments to the lenti sgRNA(MS2) _zeo backbone to form the CRISPR-Cas9 recombinant lentivirus vector; and
1.25) transforming and sequencing; wherein the *Escherichia coli* DH5a is transformed; a positive clone is screened and a sequence is identified.

The benefits of the present invention are as follow. The present invention disclosed a method of constructing a specific CRISPR-Cas9 to activate a RSPO2 gene which is applied in the research of liver fibrosis. The CRISPR-Cas9 is able to specifically activate the human RSPO2 gene expression and is able to enhance the competence of the Wnt signal pathway when transfected hepatic stellate cell, which significantly up-regulates the biomarkers α-SMA and Collagen I of liver fibrosis. The present invention adopts the CRISPR-Cas9 of the RSPO2 gene target to effectively activate the hepatic stellate cell and provide an effective way to study liver fibrosis.

BRIEF DESCRIPTION OF THE DRAWINGS

FIG. 2 is a sequencing result of a CRISPR-Cas9 of a specifically targeted RSPO2 gene plasmid transform into an *Escherichia coli* DH5a (PX458_RSPO2_1, PX458_RSPO2_2 and PX458_RSPO2_3);

FIG. 3 is a test result of 293FT cell transfecting a CRISPR-Cas9 plasmid which contains specifically targeted RSPO2 gene, collecting the transfected cell after 48 hours, PCR amplifying RSPO2 gene and T7EI enzyme digestion electrophoresis testing of the products;

FIG. 4 is a lentiviral vector sequencing result of target 1, 2 and 3 corresponding to the RSPO2 gene;

FIG. 5 illustrates QPCR (quantitative polymerase chain reaction) verifying CRISPR-Cas9 specifically activating the RSPO2 gene of the hepatic stellate cell and up-regulating a mRNA level of the RSPO2;

DETAILED DESCRIPTION OF THE PREFERRED EMBODIMENT

Figure 1:
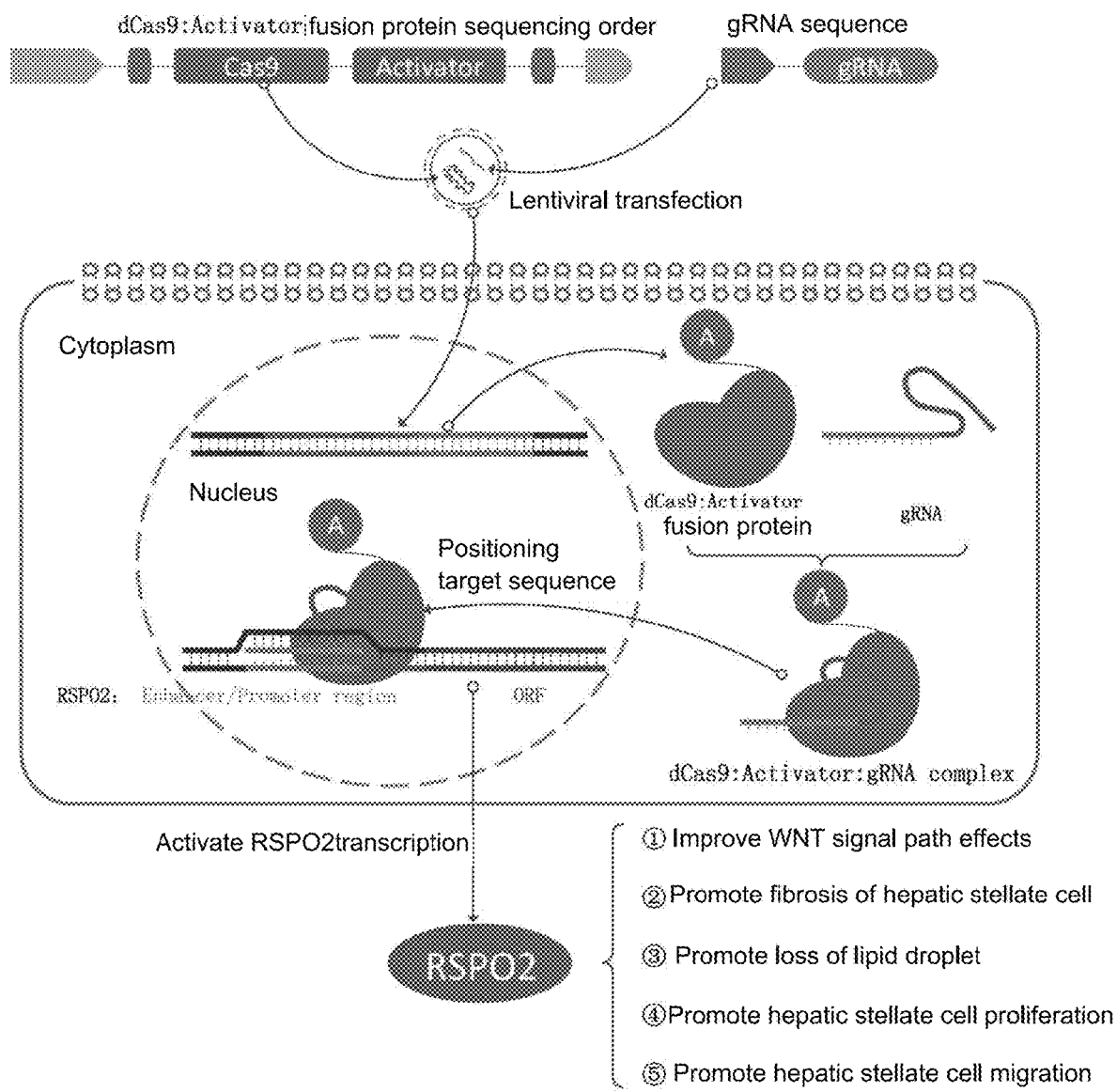
FIG. 1 illustrates the principal of CRISPR-Cas9 specifically activating a human RSPO2 gene.

Referring to the drawings, according to preferred embodiments the present invention is further illustrated. The embodiments are for explaining the present invention and not a limitation to the present invention.

The various sgRNA are able to be used in combination of two of more sgRNA. By combination, the CRISPR-Cas9 is able to target multiple targets and activate the human RSPO2 gene effectively.

The following embodiments are not independent but consecutive process. The molecular biology technologies involved in the embodiments include the cell culture, vector construction, cell transfection, clone, gene sequencing, Western blot test, PCR amplification and test and immunofluorescence. Except explained otherwise, the technologies adopted are regular technologies which are understandable by a skilled technician in the field and the instruments, reagents, plasmid, cell strain and etc. are able to be approached by a skilled technician in the field through public channel.

Embodiment 1: Designing the sgRNA Sequence

No identified principal for designing the sgRNA to ensure a highly effective CRISPRa expression. Based on the experiences, the sgRNA sequence is designed to satisfy the follow conditions:
a) a length of the sgRNA is 20 nucleotide sequences;
b) a target of the sgRNA on the RSPO2 gene locates in a promoter region;
c) the target is located on an upstream −120--75 bp of the TSS (transcription start site);
d) 5'-NGG is selected for PAM in a RSPO promoter region;
e) a sgRNA target sequence is preferred to start at G to ensure an effective U6 promoter; and
f) a format of the sgRNA target sequence is as follow:

5'-G-(19N)-NGG-3' (the sgRNA target sequence starts at G)
or 5'-(20N)-NGG-3' (the sgRNA target sequence doesn't start at G)
wherein, 19N or 20N denote 19 or 20 nucleotide sequences of the sgRNA target.

The sgRNA sequences of the targeted RSPO2 gene are designed based on the conditions, from which ten sgRNA sequences are selected as examples to illustrate the present invention. The ten sgRNA sequences are listed in the sequence list as SEQ ID NO. 2, 4, 6, 8, 10, 12, 14, 16, 18, 20; the corresponding DNA target sequences are listed in the sequence list with singular numbers SEQ ID NO. 1, 3, 5, 7, 9, 11, 13, 15, 17, 19 (wherein 1-20 is the target sequence, the last three numbers are PAM sequences).

Embodiment 2 Selecting the sgRNA Sequence

Candidate sgRNA sequences and genome database undergoes paralogy analysis by adopting Blast (www.ncbi.nlm-.nig.gov/Blast) to ensure the uniqueness of the sgRNA which is not paralogous to the gene sequences other than the human RSPO2 genes. The sgRNA sequences of highly effective and specifically activated human RSPO2 genes are selected based on the following rules:
a) the sgRNA target locates in DHSs (DNase I hypersensitive sites);
b) the sgRNA target locates in the upstream −120--75 bp of the TSS;
c) a low off-target rate.

Three sgRNA sequences corresponding to different targets of the targeted human RSPO2 genes satisfy the rules and are selected from the ten sgRNA sequences of the targeted human RSPO2 genes (corresponding to SEQ ID NO. 2, 4, 6 in the sequence list). The sgRNA target sequences and the corresponding PAM sequences are listed in the table 1 (corresponding to SEQ ID NO. 1, 3, 5 in the sequence list).

Embodiment 3 Synthesizing the Oligonucleotides of the sgRNA

Adding BsmBI cut site on two ends of the sgRNA sequences of the targeted human RSPO2 genes, comprising the following steps:
a) adding a CACC (complementary sequence of BsmBI cutting site sticky ends) and a G (to ensure an effective U6 promoter) on 5' end of targeted sequence to obtain a forward oligo based on a selected sgRNA;
b) obtaining a complementary strand of a corresponding DNA based on the selected sgRNA; adding a AAAC (complementary sequence of BsmBI cutting site sticky ends) on 5' end of the corresponding DNA sequence and adding a C on 3' end to obtain a reverse oligo;
synthesizing the forward oligo and the reverse oligo by chemical synthesis method to obtain the oligonucleotides as shown in the table 2.

Embodiment 4 Verifying Endogenous Activity of the sgRNA Targets wherein a synthesized oligonucleotides single-chain fragment (table 2) is annealed and ligated to PX458 vector plasmid (Feng zhang, Nature Protocol 2013); PX458 contains a Cas9 and a sgRNA backbone; a PX458 vector transcribes a sgRNA of the specifically targeted RSPO2 gene and a Cas9 protein that cuts the target inside a cell. The annealing and ligation process comprises the following steps:

1) phosphorylating the oligonucleotides;
phosphorylating the synthesized oligonucleotides by adopting T4 polyphosphate kinase (Takara);
2) annealing the oligonucleotides, comprising the following sub-steps:
i) establishing the following annealing reaction system (room temperature) in the sterile centrifuge tubes;

| | |
|---|---|
| forward oligo | 10 µl |
| reverse oligo | 10 µl |
| 5 × DNA annealing buffer | 10 µl |
| Dnase/Rnase-Free H2O | 20 µl | ii) incubating for 4 minutes at 95° C.; incubating for 10 minutes at 70° C.;
iii) taking out of the centrifuge tubes; placing at the room temperature for 5-10 minutes; cooling down to the room temperature;
iv) centrifuging for a short time; blending;
3) ligating to the vector;
i) PX458 plasmid is linearized by the BbsI enzyme digestion and a DNA purification kit is adopted to purify and recover an enzyme digestion product;
ii) ligating the annealing products to the vector PX458; the ligation reaction is as follow:

| | |
|---|---|
| products of the oligonucleotides annealing | 4 µl |
| products of PX458 enzyme digestion recovering | 1 µl |
| T4 ligase | 1 µl |
| Dnase/Rnase-Free H2O | 10 µl | iii) incubating for 1 hour at 16° C. to obtain vector PX458_RSPO2_1, PX458_RSPO2_2 and PX458_RSPO2_3;
4) plasmid transforming into the *Escherichia coli* DH5a, comprising the following sub-steps:
i) ice bathing the DH5a competent cell for 5 minutes at 4° C.;
ii) adding the constructed plasmids (PX458_RSPO2_1, PX458_RSPO2_2 and PX458_RSPO2_3) of 10 µl respectively; blowing even; ice bathing for 30 minutes at 4° C.;
iii) water bathing for 90 s at 42° C.; rapidly ice bathing for 3 min;
iv) adding LB bacteria culture (NaCl 1 g; peptone 1 g; yeast extract 0.5 g; dissolving in 100 ml H$_2$O; high pressure steam sterilizing) of 30 µl; blending; horizontal vibrating (180 rpm) for 1 hour at 37° C.;
v) coating the bacteria liquid of 100 µl on the LB solid culture medium (containing 1/1000 ampicillin); incubating overnight at 37° C.; and
vi) selecting 5-10 clone colony; swaying the bacterium in the LB agar containing ampicillin;
5) screening positive clone and sequencing identification, comprising the following sub-steps:
i) selecting colony PCR and initially identifying the positive clone;
the primer sequence is as follow:
upstream primer: 5'-GAGGGCCTATTTCCCATGAT-TCC-3' (SEQ ID NO:29);
amplification conditions: 10 minutes at 94° C., one cycle; 30 seconds at 94° C., 30 seconds at 55° C., 30 seconds at 72° C., 30 cycles; 6 minutes at 72° C., one cycle; and ii) screening the positive clone for further sequencing analysis; wherein the sequencing result (referring to FIG. 2) shows a successful vector construction;
6) transfecting 293FT cell; amplifying the RSPO2 gene by PCR; identifying a T7EI enzyme digestion; wherein further sub-steps are as follow:
i) transfecting the 293FT cell with the constructed vector plasmid;
ii) sorting the positive cell by a flow cytometry; and
iii) extracting the DNA of the sorted cell; amplifying the RSPO2 gene by PCR;
the primer sequences are:
upstream primer: 5'-GTTTCCTCAGGGCATTGCTT-3' (SEQ ID NO:21), as shown in the sequence list SEQ ID NO: 21;
downstream primer: 5'-TGCATTATTTCCCTGGCTGA-3' (SEQ ID NO:22), as shown in the sequence list SEQ ID NO: 22;
the amplification conditions: 3 minutes at 95° C., one cycle; 30 seconds at 55° C., 30 cycles; 6 minutes at 72° C., one cycle; and
iv) T7EI enzyme digestion identification; wherein
the recovered PCR products are identified by T7 Endonuclease I enzyme digestion and the enzyme digestion system is as follow:

| | |
|---|---|
| T7EI | 1 µl |
| buffer | 2 µl |
| PCR products | 10 µl |
| deionized water | 7 µl | water bathing for 45 minutes at 37° C.; testing the enzyme digestion products of 10 µl by the agarose gel electrophoresis; the result (referring to the FIG. 3) shows that the various targets corresponding to the RSPO2 genes mutate to a certain extend.

Embodiment 5 Constructing the Lentiviral Vector

Annealing and ligating the synthesized three pairs of oligonucleotides single-chain fragments (referring to table. 2) to the lentiviral vector which transcribes the sgRNA of the specifically targeted RSPO2 respectively. The annealing and ligating process are as follow:
1. linearizing and recovering the vector, wherein
the lentiviral vector adopts lenti sgRNA (MS2)_zeo backbone (Feng Zhang, Nature, 2014) which contains BsmBI enzyme cutting site for inserting sgRNA and a U6 promoter to control the sgRNA expression; comprising the following sub-steps
1) enzyme digestion the lenti sgRNA(MS2)_zeo backbone plasmid by BmsBI, wherein the enzyme digestion system is as follow:

| | |
|---|---|
| lenti sgRNA(MS2)_zeo backbone | 5 µl (400 ng/µl) |
| 10 × Buffer | 2 µl |
| BmsB I | 1 µl |
| Dnase/Rnase-Free H$_2$O | 12 µl |

2) incubating for 3 to 4 hours at 37° C.; and
3) recovering the enzyme digestion products by a DNA purification kit;
2. phosphorylating the oligonucleotides, wherein
phosphorylating the synthesized oligonucleotides by adopting T4 polyphosphate kinase (Takara);

3. annealing the oligonucleotides, comprising the following sub-steps:
1) establishing the following annealing reaction system (room temperature) in the sterile centrifuge tubes;

| | |
|---|---|
| forward oligo | 10 μl |
| reverse oligo | 10 μl |
| 5 × DNA annealing buffer | 10 μl |
| Dnase/Rnase-Free H2O | 20 μl |

2) incubating for 4 minutes at 95° C.; incubating for 10 minutes at 70° C.;
3) taking out of the centrifuge tubes; placing at the room temperature for 5-10 minutes; cooling down to the room temperature;
4) centrifuging for a short time; blending;
4. ligating to the vector, comprising the following sub-steps:
1) ligating the annealing products to the vector lenti sgRNA(MS2)_zeo backbone; the ligation reaction is as follow:

| | |
|---|---|
| products of the oligonucleotides annealing | 4 μl |
| products of lenti sgRNA(MS2)_zeo backbone enzyme digestion recovering | 1 μl |
| T4 ligase | 5 μl |
| Dnase/Rnase-Free H2O | 10 μl |

2) incubating for 1 hour at 16° C. to obtain lentivial vector plasmids lenti_sgRNA_RSPO2_1, lenti_sgRNA_RSPO2_2 and lenti_sgRNA_RSPO2_3;
5. transforming to the *Escherichia coli* DH5a, comprising the following sub-steps:
1) adding the ligation products (lenti_sgRNA_RSPO2_1, lenti_sgRNA_RSPO2_2 and lenti_sgRNA_RSPO2_3) of 10 μl respectively into the 100 μl DH5a competent cell; blowing even; settling in the ice for 20 minutes; water bathing for 90 s at 42° C.; rapidly ice bathing for 3 minutes; adding 500 μl LB liquid culture media; putting in the shaker 180 rpm for 1 hour at 37° C.;
2) coating the bacteria liquid of 100 μl on the LB solid culture medium (containing 1/1000 ampicillin); incubating overnight at 37° C.;
6. screening the positive clone and sequencing identification, comprising the sub-steps as follow:
1) selecting colony PCR and initially identifying the positive clone;
the primer sequence is as follow:
upstream primer: 5'-GAGGGCCTATTCCCATGATTCCTTCATAT-3' (SEQ ID NO:30);
downstream primer: 5'-CCTAGAAGGTCCATTAGCTGCAAAGATTCC-3' (SEQ ID NO:31);
amplification conditions: 10 minutes at 94° C., one cycle; 30 seconds at 94° C., 30 seconds at 55° C., 30 seconds at 72° C., 30 cycles; 6 minutes at 72° C., one cycle;
2) screening the positive clone for further sequencing analysis; wherein the sequencing result (referring to FIG. 4) shows a successful lentiviral vector construction.

Embodiment 6 Validating the Lentiviral Vector 1. inoculating the 293FT cell in the 96-well plate at the density of $2\times10^4$ cells per well; adding high glucose DMEM culture media containing 10% FBS (Fetal Bovine Serum); cultivating in a 5% CO2 incubator;
2. replacing the cell culture media with a serum-free media 2 hours before an infection;
3. transfecting the lentiviral vectors when the cell confluence reaches 70%; wherein the lentiviral vectors are divided into four groups: 1) negative control group; 2) lenti_sgRNA_RSPO2_1; 3) lenti_sgRNA_RSPO2_2; 4) lenti_sgRNA_RSPO2_3; plasmids dCAS9-VP64_GFP and lenti MS2-P65-HSF1_Hygro are added into the four groups; the reaction system is as follow:

| | |
|---|---|
| lentiviral vector plasmids | 0.1 μg/well |
| dCAS9-VP64_GFP | 0.1 μg/well |
| lenti MS2-P65-HSF1_Hygro | 0.1 μg/well |
| Lipofectamine 2000 | 0.6 μg/well |

4. transfecting for 48 hours and recovering the cells;
5. testing the fluorescence intensity of the sample by the microplate reader with an excitation of 485 nm and an emission of 533 nm;
6. calculating the fluorescence intensity fluorescence intensity=(the fluorescence intensity of the transfection group–the fluorescence intensity of the non-transfection group)/the fluorescence intensity of non-transfection group wherein the result indicates that the lentiviral vectors (lenti_sgRNA_RSPO2_1, lenti_sgRNA_RSPO2_2 and lenti_sgRNA_RSPO2_3) of the CRISPR-Cas9 system specifically targeted RSPO2 are able to effectively activate the RSPO2 gene expression.

Embodiment 7 Lentiviral Packaging

Plasmid dCAS9-VP64_GFP (Feng Zhang, Nature 2014) expresses dCAS9 and VP64 protein; plasmid lenti MS2-P65-HSF1_Hygro (Feng Zhang, Nature 2014) expresses MS2-P65-HSF1 fusion protein. The lentiviral packaging system is a four-plasmid system (Shanghai Genepharma Co., Ltd) which comprises a shuttle vector, PG-p1-VSVG, PG-P2-REV and PG-P3-RRE; wherein the shuttle vector is able to express the target gene; PG-p1-VSVG, PG-P2-REV and PG-P3-RRE contain necessary elements of the lentiviral packaging.
1. Cell strain
digesting the well developed 293T cell with 0.25% pancreatin; inoculating the 293T cell in a 10 cm cell culture dish (about $2\text{-}2.5\times10^6$ cells in each cell culture dish); cultivating the cells in the $CO_2$ incubator at 37° C.;
2. lentiviral packaging
preparing the lentiviral packaging with vector (lenti_sgRNA_RSPO2_1, lenti_sgRNA_RSPO2_2 and lenti_sgRNA_RSPO2_3), dCAS9-VP64_GFP, lenti MS2-P65-HSF1_Hygro according to the following method:
1) the reaction system of the lentiviral packaging is as follow:

| | |
|---|---|
| expression vector | 20 μg |
| PG-p1-VSVG vector | 10 μg |
| PG-P2-REV vector | 10 μg |
| PG-P3-RRE vector | 10 μg |
| serum-free Opti-MEM | 750 μl |
| RNAi-Mate | 300 μl | wherein the total regulated volume is 2.5 ml; the lentiviral packaging system is incubated for 5 minutes at a room temperature;

2) mixing 100 µl Lipofectamine2000 reagent with 2.4 ml Opti-MEM in another tube; incubating for 5 minutes at room temperature; mixing the diluted DNA and diluted Lipofectamine2000; reverse mixing for 5 minutes; incubating for 20 minutes at room temperature;
3) transforming the mixture of the DNA and the Lipofectamine2000 to the 293T cell culture media and blending; cultivating for 4-6 hours and replacing the culture media with DMEM (+10% FBS) culture media; cultivating in $CO_2$ incubator for 48 hours;
3. collecting and concentrating the lentivirus;
1) collecting the 293FT cell supernatant after transfecting for 48-72 hours (transfecting start at 0 hour);
2) centrifuging for 4000 g at 4° C. and removing the cell debris;
3) filtering the supernatant with 0.45 filter in 40 ml ultra centrifugal;
4) adding the crude extract of the lentivirus sample into the filtering cup (19 ml at the most); inserting the filtering cup into the filtrate collecting tube;
5) centrifuging in 4000×g until the concentration volume reaches the requirement, which need 10-15 minutes;
6) taking out the filtering cup after centrifuging; separating the filtering cup with the collected liquid;
7) centrifuging under 1000 g for 2 minutes;
8) obtaining the lentivirus LV_dCAS9-VP64, LV_MS2-P65-HSF1, LV_RSPO2_1, LV_RSPO2_2 and LV-RSPO2_3 from the lentivirus concentration in the sample collecting cup;
9) moving the lentivirus concentration to the lentivirus tubes after separation; storing at −80° C. for future use.
4. titrating the lentivirus;
titrating the lentivirus by adopting the quickTiter lentivirus titer kit, comprising the following steps:
1) preparing and blending the reagents according to instructions;
2) preparing two parallel holes for each lentivirus sample, standard lentivirus, blank and the control;
3) adding 100 µl deactivated lentivirus sample and standard P24 antigen into the antibody coating plates;
4) sealing the 96-well plate with the sealing film and incubating for 4 hours at 37° C.;
5) removing the sealing film, discarding the liquid in the 96-well plate and washing the plate with 250 µl 1× scrubbing solution for three times; drying the plates;
6) adding 100 µl diluted FITC marked single clone antibody for p24 in each well;
7) scaling the 96-well plate with the sealing film; placing the 96-well plate in the shaker; incubating for 1 hour at room temperature;
8) removing the sealing film, discarding the liquid in the 96-well plate and washing the plate for three times;
9) adding 100 µl diluted HRP marked single clone antibody for FITC in each well; scaling the 96-well plate with the sealing film; placing the 96-well plate in the shaker; incubating for 1 hour at room temperature;
10) removing the sealing film discarding the liquid in the 96-well plate, washing the plate for three times and rapidly go to the next step;
11) cooling the substrate solution to the room temperature; adding 100 µl substrate solution in each well including the blank plate; placing the 96-well plate on the shaker; incubating for 20-30 minutes at room temperature;
12) stopping the reaction by adding 100 µl stopping solution in each well;—testing the absorbance of each well at 450 nm wavelength by microplate reader;

calculating the amount of the lentivirus p24 protein; wherein each lentivirus particle (LP) contains around 2000 p24 molecular; obtaining the lentivirus titer according to the formula:

$$1 \text{ ng } p24 = 1.25 \times 10^7 \text{ LP};$$

table 3 various lentivirus titer

| Lentivirus | titer |
| --- | --- |
| LV_dCAS9-VP64 | $2.47 \times 10^6$ LP |
| LV_MS2-P65-HSF1 | $2.65 \times 10^6$ LP |
| LV_RSPO2_1 | $4.13 \times 10^6$ LP |
| LV_RSPO2_2 | $3.78 \times 10^6$ LP |
| LV_RSPO2_3 | $3.93 \times 10^6$ LP |

Embodiment 8 Transfecting the Human Hepatic Stellate Cell Strain 1) cultivating the human hepatic stellate cell; inoculating the cell suspension in the 12-well plate; cultivating in the 5% $CO_2$ incubator at 37° C.;
2) dividing the cell into groups when the cell confluence reaches 30% to 40%; wherein the groups are as follow: a) negative control group: for negative controlling lentivirus particle transfection cell; b) RSPO2_1 experimental group; transfecting the cell with the lentiviral vectors LV_RSPO2_1, LV_dCAS9-VP64, LV_MS2-P65-HSF1; c) RSPO2_2 experimental group; transfecting the cell with the lentiviral vectors LV_RSPO2_2, LV_dCAS9-VP64, LV_MS2-P65-HSF1; d) RSPO2_3 experimental group; transfecting the cell with the lentiviral vectors LV_RSPO2_3, LV_dCAS9-VP64, LV_MS2-P65-HSF1;
3) taking out the lentivirus stored at 4° C.; centrifuging for 20 seconds with stationary centrifugal; diluting the lentivirus with MOI 0.2 in the culture media; minimizing the volume of the culture media containing the lentivirus as long as possible to obtain a preferred transfection efficiency;
4) transfecting the lentivirus when the cell confluence reaches 70%;
a) absorbing an accurate volume of the lentivirus liquid with a pipet; adding the lentivirus liquid in the prepared culture media;
b) absorbing the culture media in the original cell culture media (if the cells grow well with a preferred density, no need to replace the culture media);
c) adding the calculated lentivirus liquid in the target cell and the control cell;
d) incubating in the $CO_2$ incubator (37° C., 5% $CO_2$) overnight after blending;
5) observing the cell after 12 hours; if no obvious cytotoxicity appears, continue the cultivation for 48 hours before replacing the culture media; if appears obvious cytotoxicity, replace the culture media immediately;
6) observing the expression of the lentivirus reporter's green fluorescent protein (GFP) 4 to 5 days after the infection; if the infection efficiency is below 50%, re-infects the cell; if the infection efficiency is over 50%, collects the cell for further test.

Embodiment 9 QPCR Test

Transfecting the human hepatic stellate cell with the constructed lentivirus as illustrated in the embodiment 7;

QPCR testing the mRNA level of the RSPO2 and the marker (α-SMA, Collagen-I) of liver fibrosis;

1) PCR primer is the upstream primer as follow:

| gene | Forward oligo | Reverse oligo |
|---|---|---|
| RSPO2 | 5'-GTTTCCTCAGG GATTGCTT-3' (SEQ ID NO: 21) | 5'-TGCATTATTTC CCTGGCTGA-3' (SEQ ID NO: 22) |
| α-SMA | 5'-GCATCTGGGTG AAAAGTGGT-3' (SEQ ID NO: 32) | 5'-GCAATGCCTCT GATTTCCAT-3' (SEQ ID NO: 33) |
| Collagen-I | 5'-CCAAATCTGTC TCCCCAGAA-3' (SEQ ID NO: 34) | 5'-TCAAAAACGAA GGGGAGATG-3' (SEQ ID NO: 35) |
| β-actin | 5'-GAAGCTGTGCT ATGTTGCTCTA-3' (SEQ ID NO: 36) | 5'-CAATAGTGATG ACCTGGCCGT-3' (SEQ ID NO: 37) |

2) extracting the RNA by Trizol; storing RNA at −80° C.;
3) determining the absorbance at 260 nm and 280 nm wavelength by the ultraviolet Spectrometer; calculating the concentration of the extracted RNA;
4) reverse transcribing and synthesizing cDNA by the reverse transcribing kit; the reaction system is as follow:

| | |
|---|---|
| 2 × RT buffer | 10 μl; |
| 6N random primer (100 pmol/μl) | 1 μl |
| RT-mix | 1 μl |
| Template (RNA) | 5 μl |
| DEPC water | 3 μl |

10 minutes at 25° C., 50 minutes at 42° C., 5 minutes at 85° C.: storing at −20° C.

5) PCR reaction system is as follow:

| | |
|---|---|
| SYBR green I | 0.5 μl |
| 2 × PCR buffer | 25 μl |
| Upstream primer(25 pmol/L) | 1 μl |
| Downstream primer(25 pmol/L) | 1 μl |
| Sample cDNA | 2 μl |
| DEPC water | 20.5 μl |

Reacting on the ABI 7500 PCR instrument;
6) PCR conditions: 4 minutes at 94° C., one cycle; 20 seconds at 94° C., 30 seconds at 60° C., 30 seconds at 72° C., 35 cycles; extending for 5 minutes at 72° C.;
7) analyzing the data with SDS software; analyzing the result by comparing the Ct value; standardizing the expression value of the target gene by β-actin.

QPCR test shows that the mRNA level of the RSPO2 of the human hepatic stellate cell and the marker of liver fibrosis α-SMA and Collagen-1 (referring to the FIG. 5) is up-regulated significantly comparing to the control group. The CRISPR-Cas9 system designed by the present invention activates the RSPO2 target gene expression and promotes the fibrogenesis of the hepatic stellate cell.

Embodiment 10 Western Blot Testing

Figure 6:
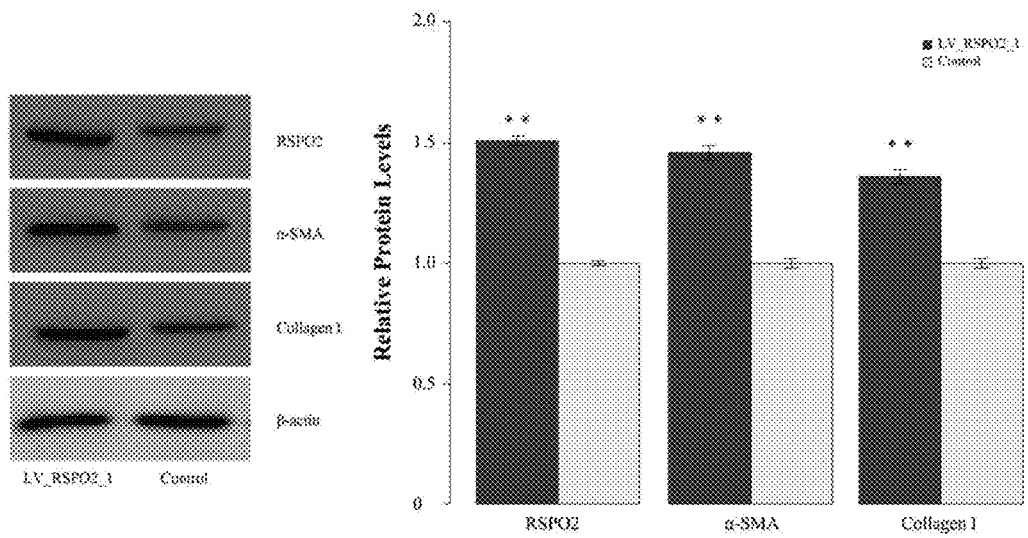
FIG. 6 illustrates Western Blot verifying CRISPR-Cas9 activating the RSPO2 gene of the hepatic stellate cell and up-regulating a RSPO2 protein level.

Taking the LV_RSPO2_1 as an example, transfecting the human hepatic stellate cell with the constructed lentivirus as illustrated in the embodiment 7; testing the expression of the RSPO2 protein in the hepatic stellate cell and the marker of liver fibrosis α-SMA and Collagen-I protein by the Western blot; comprising the following steps 1) extracting the protein of human hepatic stellate cell by RIPA lysis buffer;
2) testing the absorbance of the various wells at 562 nm wavelength by the microplate reader; calculating the protein concentration according to the standard curve;
3) separating by polyacrylamide gel electrophoresis, transmembraning and sealing with 5% skimmed milk powder; adding RSPO2 antibody (1:1000), α-SMA antibody (1:300) and Collagen-I (1:1000) respectively; incubating overnight at 4° C.;
4) adding secondary antibodies (1:2000) after washing; incubating for two hours at room temperature before ECL (electrogenerated chemiluminescence) testing; and
5) taking β-actin as the internal reference to analyze the grey scale of the various stripes by the gel image system (Bio-Rad Laboratories AB);

Western blot test shows that the expression of the RSPO2 protein of the human hepatic stellate cell and the marker of liver fibrosis α-SMA protein and Collagen-I protein (referring to the FIG. 6) is up-regulated significantly comparing to the control group. The CRISPR-Cas9 system designed by the present invention activates the RSPO2 target gene expression and promotes the fibrogenesis of the hepatic stellate cell.

Embodiment 11 Immunofluorescence Testing

Figure 7:
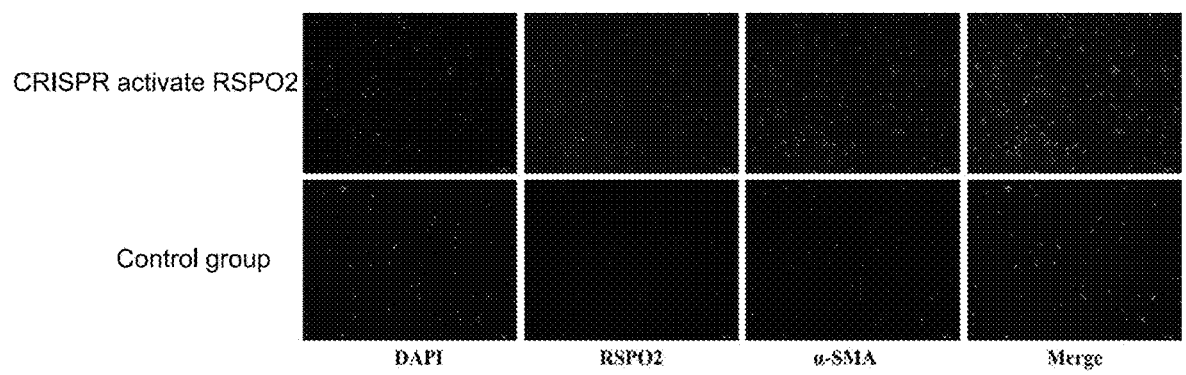
FIG. 7 illustrates immunofluorescence verifying CRISPR-Cas9 activating the target 1 of the RSPO2 gene in the hepatic stellate cell to promote the fibrogenesis of the hepatic stellate cell.

Taking the LV_RSPO2_1 as an example, transfecting the human hepatic stellate cell with the constructed lentivirus as illustrated in the embodiment 7; testing the expression of the RSPO2 protein in the hepatic stellate cell and the marker of liver fibrosis α-SMA by immunofluorescence testing; comprising the following steps:

1) discarding the culture media for the transfected hepatic stellate cell by the lentivirus LV_RSPO2_1; washing the cell with the incubated PBS for 10 minutes for two times respectively; fixing the cells for 15 minutes by 4% POM (Polyoxymethylene) at the room temperature;
2) washing the cells for 10 minutes for two times respectively by PBS; permeating the membrane with 0.1% Triton X-100 at 4° C. for 15 minutes;
3) washing the cells for 10 minutes for two times respectively by PBS; sealing the cells with 4% BSA for 30 minutes at room temperature;
4) diluting the various primary antibodies (RSPO2 and α-SMA) by 1:100; incubating overnight in the refrigerator at 4° C.;
5) washing the cells for 10 minutes for three times respectively by PBS; diluting the various secondary antibodies by 1:100; incubating for one hour at 37° C.; and
6) washing the cells for 10 minutes for three times respectively with PBS; staining the nucleus with DAPI (4',6-diamidino-2-phenylindole) and shooting with fluorescence microscope;

The immunofluorescence test shows that the expression of the RSPO2 protein and the α-SMA protein of the hepatic stellate cell are up-regulated significantly comparing to the control group (referring to the FIG. 7). The CRISPR-Cas9 system designed by the present invention activates the RSPO2 target gene expression and promotes the fibrogenesis of the hepatic stellate cell.

Embodiment 12 MTT Proliferation Testing

Taking the LV_RSPO2_1 as an example, transfecting the human hepatic stellate cell with the constructed lentivirus as illustrated in the embodiment 7; testing the proliferation of the hepatic stellate cell by MTT; comprising the following steps:
1) inoculating the human hepatic stellate cell in the 96-well culture plate; wherein the cell density of the each well is $4\times10^3$;
2) transfecting the LV_RSPO2_1 lentiviral vector in the control group as illustrated in the embodiment 4;
3) transfecting for 24 hours, 48 hours and 72 hours; adding 10 μl MTT liquid in each orifice;
4) incubating for 4 hours at 37° C.; adding 100 μl DMSO in each well; blending even; and
5) testing the absorbance at 570 nm wavelength by the microplate reader; calculating the cell survival rate.

Figure 8:
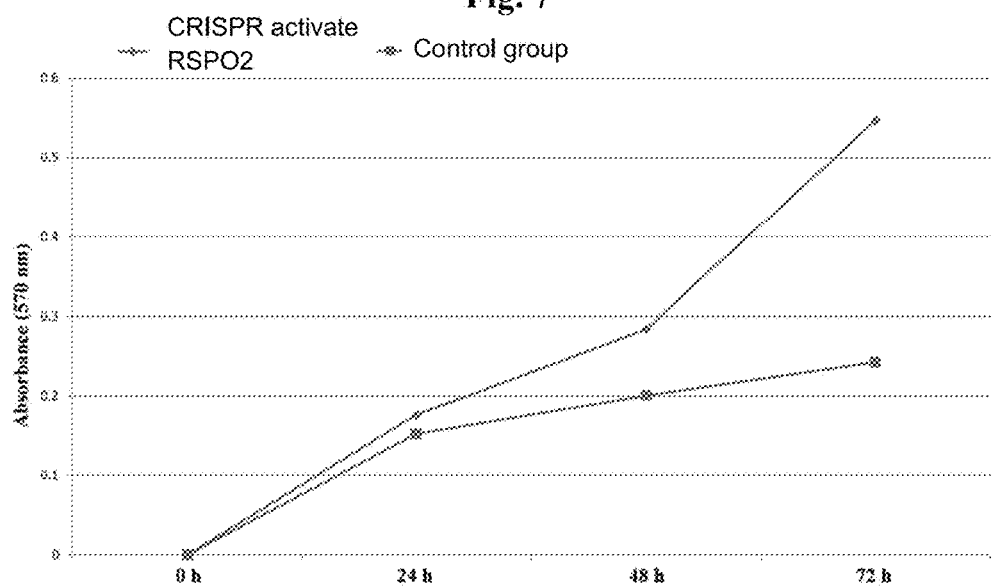
FIG. 8 illustrates MTT proliferation test verifying CRISPR-Cas9 activating the target 1 of the RSPO2 gene in the hepatic stellate cell to promote the proliferation of the hepatic stellate cell.

The MTT test shows that the proliferation of the hepatic stellate cell is up-regulated significantly comparing to the control group (referring to the FIG. 8). The CRISPR-Cas9 system designed by the present invention activates the RSPO2 target gene expression and promotes the proliferation of the hepatic stellate cell.

What is claimed is:

1. A guide RNA for a sgRNA (single guide RNA) of a specifically targeted RSPO2 (R-spondin2) gene of a CRISPR-Cas9 system, wherein said guide RNA is an RNA consisting of the nucleotide sequence of SEQ ID NO: 2.

* * * * *

SEQUENCE LISTING

<160> NUMBER OF SEQ ID NOS: 43

<210> SEQ ID NO 1
<211> LENGTH: 23
<212> TYPE: DNA
<213> ORGANISM: Artificial sequences
<220> FEATURE:
<223> OTHER INFORMATION: RSPO2 target 1 oligo sequence

<400> SEQUENCE: 1
caacgttctt taggacctca ggg                                        23

<210> SEQ ID NO 2
<211> LENGTH: 20
<212> TYPE: RNA
<213> ORGANISM: Artificial sequences
<220> FEATURE:
<223> OTHER INFORMATION: RSPO2 target 1 sgRNA sequence

<400> SEQUENCE: 2
caacguucuu uaggaccuca                                            20

<210> SEQ ID NO 3
<211> LENGTH: 23
<212> TYPE: DNA
<213> ORGANISM: Artificial sequences
<220> FEATURE:
<223> OTHER INFORMATION: RSPO2 target 2 oligo sequence

<400> SEQUENCE: 3
tttaggacct cagggaaacc ggg                                        23

<210> SEQ ID NO 4
<211> LENGTH: 20
<212> TYPE: RNA
<213> ORGANISM: Artificial sequences
<220> FEATURE:
<223> OTHER INFORMATION: RSPO2 target 2 sgRNA sequence

<400> SEQUENCE: 4
uuuaggaccu cagggaaacc                                            20

<210> SEQ ID NO 5
<211> LENGTH: 23
<212> TYPE: DNA
<213> ORGANISM: Artificial sequences
<220> FEATURE:
<223> OTHER INFORMATION: RSPO2 target 3 oligo sequence

<400> SEQUENCE: 5
tttaggaccc aggaactccg agg                                        23

<210> SEQ ID NO 6
<211> LENGTH: 20
<212> TYPE: RNA

```
<213> ORGANISM: Artificial sequences
<220> FEATURE:
<223> OTHER INFORMATION: RSPO2 target 3 sgRNA sequence

<400> SEQUENCE: 6
uuuaggaccc aggaacuccg                                              20

<210> SEQ ID NO 7
<211> LENGTH: 23
<212> TYPE: DNA
<213> ORGANISM: Artificial sequences
<220> FEATURE:
<223> OTHER INFORMATION: RSPO2 target 4 oligo sequence

<400> SEQUENCE: 7
ctccaagtta ggcgcgctgt tgg                                          23

<210> SEQ ID NO 8
<211> LENGTH: 20
<212> TYPE: RNA
<213> ORGANISM: Artificial sequences
<220> FEATURE:
<223> OTHER INFORMATION: RSPO2 target 4 sgRNA sequence

<400> SEQUENCE: 8
cuccaaguua ggcgcgcugu                                              20

<210> SEQ ID NO 9
<211> LENGTH: 23
<212> TYPE: DNA
<213> ORGANISM: Artificial sequences
<220> FEATURE:
<223> OTHER INFORMATION: RSPO2 target 5 oligo sequence

<400> SEQUENCE: 9
gtccctttgg ccctgcaaag agg                                          23

<210> SEQ ID NO 10
<211> LENGTH: 20
<212> TYPE: RNA
<213> ORGANISM: Artificial sequences
<220> FEATURE:
<223> OTHER INFORMATION: RSPO2 target 5 sgRNA sequence

<400> SEQUENCE: 10
gucccuuugg cccugcaaag                                              20

<210> SEQ ID NO 11
<211> LENGTH: 23
<212> TYPE: DNA
<213> ORGANISM: Artificial sequences
<220> FEATURE:
<223> OTHER INFORMATION: RSPO2 target 6 oligo sequence

<400> SEQUENCE: 11
ggatgaatat cttcgtaggg tgg                                          23

<210> SEQ ID NO 12
<211> LENGTH: 20
<212> TYPE: RNA
<213> ORGANISM: Artificial sequences
<220> FEATURE:
<223> OTHER INFORMATION: RSPO2 target 6 sgRNA sequence

<400> SEQUENCE: 12
ggaugaauau cuucguaggg                                              20
```

```
<210> SEQ ID NO 13
<211> LENGTH: 23
<212> TYPE: DNA
<213> ORGANISM: Artificial sequences
<223> OTHER INFORMATION: RSPO2 target 7 oligo sequence

<400> SEQUENCE: 13
gtcgtggtgg atgaatatct tgg                                          23

<210> SEQ ID NO 14
<211> LENGTH: 20
<212> TYPE: RNA
<213> ORGANISM: Artificial sequences
<220> FEATURE:
<223> OTHER INFORMATION: RSPO2 target 7 sgRNA sequence

<400> SEQUENCE: 14
gucguggugg augaauaucu                                              20

<210> SEQ ID NO 15
<211> LENGTH: 23
<212> TYPE: DNA
<213> ORGANISM: Artificial sequences
<220> FEATURE:
<223> OTHER INFORMATION: RSPO2 target 8 oligo sequence

<400> SEQUENCE: 15
tctgaatcta cggaacctgg agg                                          23

<210> SEQ ID NO 16
<211> LENGTH: 20
<212> TYPE: RNA
<213> ORGANISM: Artificial sequences
<220> FEATURE:
<223> OTHER INFORMATION: RSPO2 target 8 sgRNA sequence

<400> SEQUENCE: 16
ucugaaucua cggaaccugg                                              20

<210> SEQ ID NO 17
<211> LENGTH: 23
<212> TYPE: DNA
<213> ORGANISM: Artificial sequences
<220> FEATURE:
<223> OTHER INFORMATION: RSPO2 target9 oligo sequence

<400> SEQUENCE: 17
tccgtcggat ctgaatctac cgg                                          23

<210> SEQ ID NO 18
<211> LENGTH: 20
<212> TYPE: RNA
<213> ORGANISM: Artificial sequences
<220> FEATURE:
<223> OTHER INFORMATION: RSPO2 target 9 sgRNA sequence

<400> SEQUENCE: 18
uccgucggau cugaaucuac                                              20

<210> SEQ ID NO 19
<211> LENGTH: 23
<212> TYPE: DNA
<213> ORGANISM: Artificial sequences
<220> FEATURE:
<223> OTHER INFORMATION: RSPO2 targe 10 oligo sequence
```

```
<400> SEQUENCE: 19
tcaacgttct ttaggacctc agg                                          23

<210> SEQ ID NO 20
<211> LENGTH: 20
<212> TYPE: RNA
<213> ORGANISM: Artificial sequences
<220> FEATURE:
<223> OTHER INFORMATION: RSPO2 target 10 sgRNA sequence

<400> SEQUENCE: 20
ucaacguucu uuaggaccuc                                              20

<210> SEQ ID NO 21
<211> LENGTH: 20
<212> TYPE: DNA
<213> ORGANISM: Artificial sequences
<220> FEATURE:
<223> OTHER INFORMATION: RSPO2 forward primer of gene

<400> SEQUENCE: 21
gtttcctcag ggcattgctt                                              20

<210> SEQ ID NO 22
<211> LENGTH: 20
<212> TYPE: DNA
<213> ORGANISM: Artificial sequences
<220> FEATURE:
<223> OTHER INFORMATION: RSPO2 reverse primer of gene

<400> SEQUENCE: 22
tgcattattt ccctggctga                                              20

<210> SEQ ID NO 23
<211> LENGTH: 25
<212> TYPE: DNA
<213> ORGANISM: Artificial sequences
<220> FEATURE:
<223> OTHER INFORMATION: forward oligo(1)

<400> SEQUENCE: 23
caccgcaacg ttctttagga cctca                                        25

<210> SEQ ID NO 24
<211> LENGTH: 25
<212> TYPE: DNA
<213> ORGANISM: Artificial sequences
<220> FEATURE:
<223> OTHER INFORMATION: reverse oligo(1)

<400> SEQUENCE: 24
aaactgaggt cctaaagaac gttgc                                        25

<210> SEQ ID NO 25
<211> LENGTH: 25
<212> TYPE: DNA
<213> ORGANISM: Artificial sequences
<220> FEATURE:
<223> OTHER INFORMATION: forward oligo(2)

<400> SEQUENCE: 25
caacgtttag gacctcaggg aaacc                                        25

<210> SEQ ID NO 26
<211> LENGTH: 25
<212> TYPE: DNA
<213> ORGANISM: Artificial sequences
```

```
<220> FEATURE:
<223> OTHER INFORMATION: reverse oligo(2)

<400> SEQUENCE: 26
aaacggtttc cctgaggtcc taaac                                          25

<210> SEQ ID NO 27
<211> LENGTH: 25
<212> TYPE: DNA
<213> ORGANISM: Artificial sequences
<220> FEATURE:
<223> OTHER INFORMATION: forward oligo(3)

<400> SEQUENCE: 27
caccgtttag gacccaggaa ctccg                                          25

<210> SEQ ID NO 28
<211> LENGTH: 25
<212> TYPE: DNA
<213> ORGANISM: Artificial sequences
<220> FEATURE:
<223> OTHER INFORMATION: reverse oligo(3)

<400> SEQUENCE: 28
aaaccggagt tcctgggtcc taaac                                          25

<210> SEQ ID NO 29
<211> LENGTH: 23
<212> TYPE: DNA
<213> ORGANISM: Artificial sequences
<220> FEATURE:
<223> OTHER INFORMATION: upstream primer

<400> SEQUENCE: 29
gagggcctat ttcccatgat tcc                                            23

<210> SEQ ID NO 30
<211> LENGTH: 29
<212> TYPE: DNA
<213> ORGANISM: Artificial sequences
<220> FEATURE:
<223> OTHER INFORMATION: upstream primer

<400> SEQUENCE: 30
gagggcctat tcccatgatt ccttcatat                                      29

<210> SEQ ID NO 31
<211> LENGTH: 30
<212> TYPE: DNA
<213> ORGANISM: Artificial sequences
<220> FEATURE:
<223> OTHER INFORMATION: downstream primer

<400> SEQUENCE: 31
cctagaaggt ccattagctg caaagattcc                                     30

<210> SEQ ID NO 32
<211> LENGTH: 20
<212> TYPE: DNA
<213> ORGANISM: Artificial sequences
<220> FEATURE:
<223> OTHER INFORMATION: Forward oligo of a-SMA

<400> SEQUENCE: 32
gcatctgggt gaaaagtggt                                                20

<210> SEQ ID NO 33
<211> LENGTH: 20
```

```
<212> TYPE: DNA
<213> ORGANISM: Artificial sequences
<220> FEATURE:
<223> OTHER INFORMATION: Reverse oligo of a-SMA

<400> SEQUENCE: 33
gcaatgcctc tgatttccat                                                 20

<210> SEQ ID NO 34
<211> LENGTH: 20
<212> TYPE: DNA
<213> ORGANISM: Artificial sequences
<220> FEATURE:
<223> OTHER INFORMATION: Forward oligo of Collagen-I

<400> SEQUENCE: 34
ccaaatctgt ctccccagaa                                                 20

<210> SEQ ID NO 35
<211> LENGTH: 20
<212> TYPE: DNA
<213> ORGANISM: Artificial sequences
<220> FEATURE:
<223> OTHER INFORMATION: Reverse oligo of Collagen-I

<400> SEQUENCE: 35
tcaaaaacga aggggagatg                                                 20

<210> SEQ ID NO 36
<211> LENGTH: 22
<212> TYPE: DNA
<213> ORGANISM: Artificial sequences
<220> FEATURE:
<223> OTHER INFORMATION: Forward oligo of b-actin

<400> SEQUENCE: 36
gaagctgtgc tatgttgctc ta                                              22

<210> SEQ ID NO 37
<211> LENGTH: 21
<212> TYPE: DNA
<213> ORGANISM: Artificial sequences
<220> FEATURE:
<223> OTHER INFORMATION: Reverse oligo of b-actin

<400> SEQUENCE: 37
caatagtgat gacctggccg t                                               21

<210> SEQ ID NO 38
<211> LENGTH: 289
<212> TYPE: DNA
<213> ORGANISM: Artificial sequences
<220> FEATURE:
<223> OTHER INFORMATION: Sequencing result of PX458_RSPO2_1

<400> SEQUENCE: 38
ttcgatttct tggctttata tatcttgtgg aaaggacgaa acaccgcaac gttctttagg     60
acctcgtttt agagctaggc caacatgagg atcacccatg tctgcagggc ctagcaagtt   120
aaaataaggc tagtccgtta tcaacttggc caacatgagg atcacccatg tctgcagggc   180
caagtggcac cgagtcggtg cttttttttgg atcctgcaaa gatggataaa gttttaaaca   240
gagaggaatc tttgcagcta atggaccttc taattggctc cggtgggcc                289

<210> SEQ ID NO 39
```

```
<211> LENGTH: 289
<212> TYPE: DNA
<213> ORGANISM: Artificial sequences
<220> FEATURE:
<223> OTHER INFORMATION: Sequencing result of PX458_RSPO2_2

<400> SEQUENCE: 39
ttcgattctt ggctttatat atcttgtgga aggacgaaa caacgtttag gacctcaggg      60
aaacgtttta gagctagaaa tagcaagtta aaataaggct agtccgttat caacttgaaa    120
aagtggcacc gagtcggtgc ttttttgttt tagagctaga aatagcaagt taaaataagg    180
ctagtccgtt tttagcgcgt gcgccaattc tgcagacaaa tggctctaga ggtacccgtt    240
acataactta cggtaaatgg cccgcctggc tgaccgccca acgagtcca               289

<210> SEQ ID NO 40
<211> LENGTH: 290
<212> TYPE: DNA
<213> ORGANISM: Artificial sequences
<220> FEATURE:
<223> OTHER INFORMATION: Sequencing result ofPX458_RSPO2_3

<400> SEQUENCE: 40
ttcgatttct tggctttata tatcttgtgg aaaggacgaa acaccgttta ggacccagga     60
actccgtttt agagctagaa atagcaagtt aaaataaggc tagtccgtta tcaacttgaa    120
aaagtggcac cgagtcggtg cttttttgtt ttagagctag aaatagcaag ttaaaataag    180
gctagtccgt ttttagcgcg tgcgccaatt ctgcagacaa atggctctag aggtacccgt    240
tacataactt acggtaaatg gcccgcctgg ctgaccgccc aacgacaggc               290

<210> SEQ ID NO 41
<211> LENGTH: 283
<212> TYPE: DNA
<213> ORGANISM: Artificial sequences
<220> FEATURE:
<223> OTHER INFORMATION: Lentiviral vector sequencing result of target 1
      corresponding to the RSPO2 gene

<400> SEQUENCE: 41
cgatttcttg gctttatata tcttgtggaa aggacgaaac accgcaacgt tctttaggac     60
ctcgttttag agctaggcca acatgaggat cacccatgtc tgcagggcct agcaagttaa    120
aataaggcta gtccgttatc aacttggcca acatgaggat cacccatgtc tgcagggcca    180
agtggcaccg agtcggtgct ttttttggat cctgcgtatt tcggttttg gggccgcggg    240
cggcgacggg gcccgtgcgt cccagcgcac atgttcggcg cct                      283

<210> SEQ ID NO 42
<211> LENGTH: 283
<212> TYPE: DNA
<213> ORGANISM: Artificial sequences
<220> FEATURE:
<223> OTHER INFORMATION: Lentiviral vector sequencing result of target 2
      corresponding to the RSPO2 gene

<400> SEQUENCE: 42
cgatttcttg gctttatata tcttgtggaa aggacgaaac aacgtttagg acctcaggga     60
aacgttttag agctaggcca acatgaggat cacccatgtc tgcagggcct agcaagttaa    120
aataaggcta gtccgttatc aacttggcca acatgaggat cacccatgtc tgcagggcca    180
agtggcaccg agtcggtgct ttttttggat cctgcgtatt tcggttttg gggccgcggg    240
cggcgacggg gcccgtgcgt cccagcgcac atgttcggcg cct                      283
```

```
<210> SEQ ID NO 43
<211> LENGTH: 283
<212> TYPE: DNA
<213> ORGANISM: Artificial sequences
<220> FEATURE:
<223> OTHER INFORMATION: Lentiviral vector sequencing result of target 3
      corresponding to the RSPO2 gene

<400> SEQUENCE: 43
cgatttcttg gctttatata tcttgtggaa aggacgaaac accgtttagg acccaggaac       60
tccgttttag agctaggcca acatgaggat cacccatgtc tgcagggcct agcaagttaa      120
aataaggcta gtccgttatc aacttggcca acatgaggat cacccatgtc tgcagggcca      180
agtggcaccg agtcggtgct tttttggat cctgcgtatt tcggttttg gggccgcggg        240 cggcgacggg gcccgtgcgt cccagcgcac atgttcggcg cct                        283
```